United States Patent
Yu et al.

(10) Patent No.: US 10,081,823 B2
(45) Date of Patent: Sep. 25, 2018

(54) TREATMENT METHOD FOR BIOMASS TO MAXIMIZE SUGAR YIELD, AND ADDITIVE USED IN SAME

(75) Inventors: Ju Hyun Yu, Daejeon (KR); Chan Duck Jung, Gwangju (KR); In Yong Eom, Chungcheongbuk-do (KR); Kyung Sik Hong, Daejeon (KR); Bong Keun Song, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 13/997,492

(22) PCT Filed: Dec. 23, 2011

(86) PCT No.: PCT/KR2011/010044
§ 371 (c)(1),
(2), (4) Date: Jun. 24, 2013

(87) PCT Pub. No.: WO2012/087068
PCT Pub. Date: Jun. 28, 2012

(65) Prior Publication Data
US 2013/0288312 A1 Oct. 31, 2013

(30) Foreign Application Priority Data

Dec. 24, 2010 (KR) ............... 10-2010-0134405
Nov. 2, 2011 (KR) ............... 10-2011-0113201

(51) Int. Cl.
*C12P 19/02* (2006.01)
*C13K 1/02* (2006.01)
*C12P 19/14* (2006.01)

(52) U.S. Cl.
CPC ......... *C12P 19/02* (2013.01); *C13K 1/02* (2013.01); *C12P 19/14* (2013.01); *C12P 2201/00* (2013.01)

(58) Field of Classification Search
None
See application file for complete search history.

(56) References Cited

U.S. PATENT DOCUMENTS

| | | | | |
|---|---|---|---|---|
| 4,420,612 A * | 12/1983 | Aiba et al. | ............... | 536/102 |
| 2009/0137013 A1* | 5/2009 | Schmid | ............... | C12N 1/12 |
| | | | | 435/134 |
| 2009/0162892 A1* | 6/2009 | Pompejus et al. | ............... | 435/67 |
| 2009/0239288 A1* | 9/2009 | Li | ............... | C12M 21/12 |
| | | | | 435/262 |
| 2010/0113764 A1* | 5/2010 | Blair | ............... | C07H 3/02 |
| | | | | 536/123 |
| 2010/0126501 A1* | 5/2010 | Takeshima | ............... | C13K 1/04 |
| | | | | 127/37 |
| 2010/0159522 A1 | 6/2010 | Cirakovic | | |
| 2010/0297718 A1* | 11/2010 | Deinhammer | ............... | 435/160 |

FOREIGN PATENT DOCUMENTS

| | | |
|---|---|---|
| KR | 10-0318755 B1 | 12/2001 |
| KR | 20100119018 A | 11/2010 |
| KR | 20100125845 A | 12/2010 |
| WO | 2009/058276 A1 | 5/2009 |
| WO | WO2009058276 * | 5/2009 |
| WO | 2010/113129 A2 | 10/2010 |

OTHER PUBLICATIONS

Parajo et al. "Charcoal Adsorption of Wood Hydrolysates for Improving their Fermentability: Influence of the Operational Conditions" Bioresource Technology 57(1996) 179-185.*
Jose Diz, et al; "Xylitol Production for *Eucalyptus* Wood Hydrolysates in Low-Cost Fermentation Media", Food Technol. Biotechnol.; vol. 40, No. 3; pp. 191-197; Jul.-Sep. 2002.
J.C. Parajo, et al; "Charcoal Adsorption of Wood Hydrolysates For Improving Their Fermentability: Influence of the Operationai Conditions", Bioresouroe Technology, vol. 57, Issue 2, Aug. 1996, pp. 179-185.
Eva Palmqvist, et al; "Simultaneous detoxification and enzyme production of hemicellulose hydrolysates obtained after steam pretreatment", Enzyme and Microbial Technology, vol. 20; Issue 4, Mar. 1997, pp. 286-293.
Edgardo Araque, et al; "Evaluation of organosolv pretreatment for the conversion of *Pinus radiata* D. Don to ethanol", Enzyme and Microbial Technology, vol. 43, Issue 2, Aug. 2008, pp. 214-219.
Charles E. Wyman, et al; "Comparative data on effects of leading pretreatments and enzyme loadings and formulations on sugar yields from different switchgrass sources", Bioresource Technology; vol. 102, Issue 24, EPub Jun. 21, 2011; pp. 11052-11062.
International Search Report dated Jun. 1, 2012; PCT/KR2011/010044.
Adina-Elena Segneanu, et al; "Combined Microwave-Acid Pretreatment of the Biomass", Intech, Published Jul. 27, 2011, 17 pages.

* cited by examiner

*Primary Examiner* — Blaine Lankford
(74) *Attorney, Agent, or Firm* — The PL Law Group, PLLC

(57) ABSTRACT

Disclosed is a treatment method of biomass to maximize sugar yield, which uses a specific additive which can effectively adsorb lignin-derived compounds and various inhibitors of the enzymatic activity to promote saccharification of cellulose catalyzed by cellulose hydrolases, and thus can maximize sugar yield from pretreated biomass.

18 Claims, No Drawings

TREATMENT METHOD FOR BIOMASS TO MAXIMIZE SUGAR YIELD, AND ADDITIVE USED IN SAME

FIELD OF THE INVENTION

The present invention relates to a treatment method for biomass to maximize a sugar yield by using a specific additive during pretreatment and enzymatic saccharification processes, and an additive used same.

BACKGROUND OF THE INVENTION

In recent years, significant research efforts have been made worldwide to develop transportation fuels and commodity raw materials from renewable biomass to effectively deal with the depletion of petrochemical fuels and global warming caused by greenhouse gases, and continuous attempts are being made to introduce such applications to the fuel production.

Biomass, which is believed to be a sustainable source of energy, includes lignocellulosic biomass which mainly includes phanerophytes and algal biomass which mainly includes algae that grows in water. Main components of such biomass include: cellulose including glucose, which is a primary nutrient for fermenting strains of the fermentative processes of preparing bioalcohols such as bioethanol and biobutanol; hemicelluloses mainly including pentoses such as xylose, which is not favored by fermenting microorganisms, but is a raw material for xylitol; and lignin which is currently used mainly as a heat source in the biomass production processes, but is getting more attention due to its usability in benzene ring compounds. However, each component of the biomass is delicately fused to one another and interconnected by various chemical bonds, and hence, the biomass in its natural state may not be easily obtained by fractionating the biomass into each component.

Accordingly, in the case of the lignocellulosic biomass, the biomass is first pulverized into a powder to make each component easier for fractionation, and then the powder is subjected to a biomass pretreatment process, which disintegrates the tissue by using various physiochemical methods, followed by enzymatic saccharification using a hydrolase or simultaneous saccharification and cofermentation of resulting products to obtain sugars.

Conventional methods that are generally used for a biomass pretreatment process include autohydrolysis (or hydrothermolysis), dilute acid pretreatment, lime pretreatment, ammonia pretreatment (ARP, etc.), steam explosion, and the like. During the pretreatment process, hemicellulose or lignin from a lignocellulosic biomass is dissolved to expose cellulose, and the lignin is known as the main obstacle that decreases the sugar yield. Previous researches in this field suggest that the dissolved lignin from the pretreatment process may directly inhibit enzymatic activities during an enzymatic saccharification process. Also, the dissolved lignin is readsorbed to a surface of the cellulose during a recrystallization process of the lignin to not only physically block the enzymes from coming into contact with the surface of the cellulose, but also irreversibly adsorb the enzymes to the surface of the lignin and inactivate the enzymes. For these reasons, lignin is known to decrease the conversion rate of cellulose to glucose.

Autohydrolysis (hydrothermolysis) or dilute acid pretreatment in which pretreatment effects are generated due to hydrolysis of hemicelluloses by acid catalysis at high temperature and dissolution and release of a portion of lignin as a water soluble component, has a big difference between pretreatment conditions for maximizing yield of the released hemicellulose and pretreatment conditions for maximizing glucose yield through a final enzymatic saccharification. The two pretreatment steps are typically necessary to maximize the sugar yield. However, if a median value of the two different pretreatment conditions is taken so as to achieve a high sugar yield with only one pretreatment step, the pretreatment may not only produce a large amount of furfural, which is known as an inhibitor of the fermentation strains due to an excessive degradation of hemicellulose, but also decrease the conversion rate of cellulose to glucose.

To resolve the problems, Edgardo et al. have developed a pretreatment method of dissolving lignin by adding an organic solvent during the biomass pretreatment process (see Edgardo et al., *Enzyme and Microbial Technology*, 2008, 43:214-219; U.S. Patent Publication No. 2010-0159522, Organosolve and ozone treatment of biomass to enhance enzymatic saccharification), however, the method still requires substantial improvements in terms of recovery rate of the solvent and cost of the processes, etc.

Also, as another alternative method of enhancing the sugar yield by enzymatic saccharification after the biomass pretreatment, there is a method of separating a supernatant liquid from a pretreated solid component of pretreated materials, and washing the solid component thus obtained with an excessive amount of warm water to remove various impurities including decomposed materials of lignin (see Charles E. Wyman et al., *Bioresource Technology*, 2011, Article in press, Comparative data on effects of reading pretreatments and enzyme loadings and formulations on sugar yields from different switchgrass sources). However, this method requires a phase separation process, a number of washing processes, a large scale wastewater treatment process, and the like, and thus, a drastic increase in the production cost is inevitable.

Therefore, the present inventors have endeavored to enhance the sugar yield from biomass and have found that the sugar yield may be increased when a specific additive is used in at least one of the biomass pretreatment process and enzymatic saccharification process, and thus accomplished the present invention.

SUMMARY OF THE INVENTION

Accordingly, it is an object of the present invention to provide a treatment method of biomass to maximize sugar yield from a biomass by a pretreatment process and an enzymatic saccharification process, or simultaneous saccharification and cofermentation.

It is another object of the present invention to provide a pretreatment additive for maximizing a sugar yield from a biomass.

It is a further object of the present invention to provide a saccharification additive for maximizing a sugar yield from a biomass.

In accordance with an aspect thereof, the present invention provides a treatment method of biomass comprising the steps of:

Suspending a biomass in water or an acidic aqueous solution to perform a pretreatment process of autohydrolysis or acid pretreatment and prepare a suspension; and subjecting the suspension to an enzymatic saccharification, wherein an additive selected from the group consisting of natural silicate mineral, artificial silicate mineral, zirconia, heat-resistant organic polymer, activated carbon, and a mixture thereof is added to at least one of the pretreatment process or the enzymatic saccharification.

In accordance with another aspect thereof, the present invention provides a biomass pretreatment additive selected from the group consisting of natural silicate mineral, artificial silicate mineral, zirconia, heat-resistant organic polymer, activated carbon, and a mixture thereof.

In accordance with a further aspect thereof, the present invention provides a biomass saccharification additive selected from the group consisting of natural silicate mineral, artificial silicate mineral, zirconia, heat-resistant organic polymer, activated carbon, and a mixture thereof.

The method of the present invention may effectively adsorb a lignin-derived material and various materials inhibiting enzymatic activity using a specific additive, thereby promoting enzymatic saccharification or simultaneous saccharification and fermentation, for example, the saccharification of cellulose by cellulase. Therefore, it is possible to maximize the yield of sugar obtained from biomass.

DETAILED DESCRIPTION OF THE INVENTION

Hereinafter, the present invention is described in detail.

The treatment method of biomass in accordance with the present invention comprises the steps of suspending biomass in water or an acidic aqueous solution to perform a pretreatment process of autohydrolysis or acid pretreatment and prepare a suspension; and subjecting the suspension to enzymatic saccharification, wherein an additive selected from the group consisting of natural silicate mineral, artificial silicate mineral, zirconia, heat-resistant organic polymer, activated carbon, and a mixture thereof is added to at least one of the pretreatment process or the enzymatic saccharification.

As used herein, the term "pretreatment" of biomass refers to a processing of the pulverized biomass prior to enzymatic hydrolysis process of a biomass so that the biomass may react with enzymes thoroughly, and a preceding step to a monosaccharification process by using cellulases or simultaneous saccharification and cofermentation that is carried out by simultaneously using enzymes and fermenting strains. In other words, the term refers to a process in which the biomass powders are dispersed in water or an acid aqueous solution, and agitated in a sealed container, followed by steaming by adding heat to the container.

Also, as used herein, the term "enzymatic saccharification" refers to a process for converting cellulose and hemicellulose contained in the pretreated biomass into monosaccharides such as glucose, xylose, and the like by using so-called cellulase complex enzymes including cellulases, hemicellulases, xylanase, arabinase, and the like (e.g. a mixture of Celluclast 1.5 O (Novozymes Korea) and Novozyme 188 or a mixture of Cellic CTec2 and Cellic HTec2).

In one embodiment of the present invention, the additive in accordance with the present invention may be added to the pretreatment process. This method includes the process in which the suspension including the additive of the present invention is heated and then rapidly cooled down to room temperature. More specifically, the sugar yield may be maximized by a treatment method including the steps of:

(a) suspending biomass in water or an acidic aqueous solution, adding the additive in accordance with the present invention to prepare a suspension, agitating and heating the suspension to a certain temperature, maintaining at the temperature for a certain amount of time, and rapidly cooling the suspension to room temperature to terminate the biomass pretreatment reaction and prepare pretreated materials; and (b) agitating the pretreated materials while adjusting temperature and acidity within a certain range, adding enzymes to the pretreated materials while uniformly maintaining the temperature and the acidity to perform saccharification and maximize the sugar yield.

In step (a), the suspension including the additive may be heated to a temperature in a range of about 160° C. to about 230° C. and maintained at the temperature for about 2 seconds to about 24 hours, and then rapidly cooled down to room temperature.

In another embodiment of the present invention, the additive in accordance with the present invention may be added in enzymatic saccharification or simultaneous saccharification and cofermentation process. This method includes the process of adding the additive of the present invention to the pretreated materials prepared from a conventional pretreatment process, and then agitating the pretreated materials for a certain amount of time, followed by adding enzymes thereto for the enzymatic saccharification. More specifically, the sugar yield may be maximized by a treatment method comprising the steps of:

(a) suspending biomass in water or an acidic aqueous solution, adding the additive of the present invention to prepare a suspension, agitating and heating the suspension to a certain temperature, maintaining at the temperature for a certain amount of time, and rapidly cooling the suspension to room temperature to terminate the biomass pretreatment reaction and prepare pretreated materials; and (b) agitating the pretreated biomass while adjusting temperature and acidity within a certain range, adding enzymes to the pretreated materials while uniformly maintaining the temperature and the acidity to perform saccharification and maximize the sugar yield.

In still another embodiment of the present invention, the additive in accordance with the present invention may be used in both the pretreatment process and the enzymatic saccharification process.

The additive used in the pretreatment process of the present invention is referred to as a "pretreatment additive." Similarly, the additive used in the enzymatic saccharification process is referred to as an "enzymatic saccharification additive" or "saccharification additive".

The additive used in the method of the present invention is selected from the group consisting of natural silicate mineral, artificial silicate mineral, zirconia, heat-resistant organic polymer, activated carbon, and a mixture thereof.

Examples of the natural silicate mineral include diatomite (diatomaceous earth), Fuller's earth (calcium bentonite or attapulgite), mica, zeolite, kaolinite, talc, pyrophyllite, sand, and a mixture thereof; and examples of the artificial silicate mineral include a powder or granule prepared by using one of or mixing two or more of natural silicate minerals, or a sintered material prepared by forming the powder into a granule and sintering the granule at high temperature, glass bead, and synthetic zeolite. However, examples are not limited thereto, and any silicate mineral having hydrophilic surfaces but does not dissolve in water may be used in the present invention.

The heat-resistant organic polymer that may be used as the additive of the present invention includes any organic polymer having a transition temperature of 230° C. or greater, and a particular example of the organic polymer includes polytetrafluoroethylene (PTFE, Teflon). Also, another example of the organic additive includes an activated carbon.

The pretreatment additive or the enzymatic saccharification additive of the present invention may be a particulate, powdery, or granulate additive. The particulate or powdery additive has a large surface area, and thus, the sugar yield is enhanced compared to a granulate additive. The powdery additive may be prepared by simply pulverizing a silicate mineral, zirconia, a heat-resistant organic polymer, and activated carbon; and the granulate additive may be prepared by pulverizing the above materials until they form granules. The granules may also be prepared by molding the powder or sintering the powder at high temperature such that the granules do not change in shape during pretreatment and saccharification processes of the biomass.

In the present invention, there is no specific limit on the amount of the additive used. However, it is preferable to use about 0.001 to about 10 times the dry weight of the biomass. But, considering the efficiency of the pretreatment or saccharification of the biomass, it is preferable to use about 0.001 times to about 5 times the dry weight of the biomass.

The treatment method of biomass in accordance with the present invention is not different from a conventional method, except for adding the above-described additives to the suspension containing the biomass and then agitating the suspension for a homogeneous reaction, or adding the above-described additives to the pretreated material and agitating the pretreated material at a temperature in a specific range, e.g., in a range of room temperature to about 100° C., for a specific amount of time, e.g., about 2 seconds to about 24 hours, adding an acid or a base to adjust to a pH of about 2 to about 9 while agitating, cooling down to a temperature in a range of about 40° C. to about 60° C., and then adding hydrolases. The treatment method using the biomass additive of the present invention may be applicable to both autohydrolysis (hydrothermolysis) and acid pretreatment which operate based on an acid-catalyzed hydrolysis reaction.

Specific examples of the biomass used in the treatment method of the present invention include: agricultural by-products such as sunflower stalk, corn stover, bagasse, palm residue, rice straw, barley straw, and wheat straw; forest trees such as yellow poplar, willow, spruce, and byproducts thereof; and energy crops such as miscanthus, reed, and switchgrass, but the examples are not limited thereto. The biomass may be used in a pulverized form as typically used in the production of bioalcohols such as bioethanol or biobutanol, or in the pretreatment process for biorefinery which is used for preparing desired chemical materials from the biomass. In other words, the biomass may be used in a pulverized or a powdered form.

In step (a) of the treatment method of the present invention, the weight ratio of biomass to water or an acid aqueous solution in the suspending the biomass in water or an acidic aqueous solution may be adjusted to that of conventional pretreatment process, e.g., in a range of about 1:99 to about 30:70. The range of the weight ratio may be narrowed to precisely control the pretreatment temperature and uniformly mix the reactants, e.g., in a range of about 1:99 to about 20:80.

During the biomass pretreatment process, the main temperature at which the reaction occurs and the retention time may differ depending on the type of biomass used and the method of pretreatment used, i.e., a batch pretreatment or a continuous pretreatment; however, the biomass suspension may be typically heated to a temperature ranging from about 160° C. to about 230° C., and maintained at the temperature for about 2 seconds to about 24 hours. In order to maximize the sugar yield or the saccharification rate, however, conditions of the temperature and the retention time between the conditions that enable the maximal hemicellulose (or xylose as a monosaccharide) recovery rate and the conditions that enable the maximal glucose recovery rate when pretreated without adding the additive of the present invention is preferable.

In step (b) of the treatment method of the present invention, there is no specific limit on the temperature or the agitation time of the mixture when the saccharification additive is added to the pretreated material and then agitated. However, to facilitate adsorption of enzymatic activity inhibitors to the saccharification additive and for an early termination of the adsorption reaction, the mixture is agitated at a temperature in a specific range e.g., in a range of room temperature to about 100° C., for a specific amount of time, e.g., about 2 seconds to about 24 hours, an acid or a base is added to the mixture to adjust pH to about 2 to about 9 while the mixture agitated, the mixture is cooled to the temperature of about 40° C. to about 60° C., then the additives are added to the mixture for a saccharification to improve sugar yield. The adjustment range of the acidity may differ depending on the type of the additive used.

Therefore, the treatment method of biomass in accordance with the present invention may promote enzymatic saccharification or simultaneous saccharification and cofermentation, e.g., cellulose saccharification by cellulases, and thus may maximize the sugar yield from biomass (see Examples).

Meanwhile, the present invention provides a pretreatment additive selected from the group consisting of a natural silicate mineral, an artificial silicate mineral, zirconia, a heat-resistant organic polymer, activated carbon, and a mixture thereof.

Further, the present invention provides a saccharification additive selected from the group consisting of a natural silicate mineral, an artificial silicate mineral, zirconia, a heat-resistant organic polymer, activated carbon, and a mixture thereof.

Each component used in the additive is the same as described above.

Hereinafter, the present invention is described in greater detail. The following Examples are given for the purpose of illustration only, and are not intended to limit the scope of the invention.

Example 1: Pretreatment and Enzymatic Saccharification of Sunflower Stalk Using Pretreatment Additive (1)

1 g of sunflower stalk powder of known chemical composition was introduced to a small scale reactor having a capacity of 100 mL, and 20 mL of water was added thereto. 1 g of each of the pretreatment additive listed in Table 1 was added to the reactor along with a stir bar, then, the reactor was sealed, placed in an oil bath, and then heated. When the thermometer placed in the small scale reactor indicated an initial temperature of 180° C., the temperature of the reactor was maintained at 180±1° C. for 40 minutes, then the reactor was removed from the bath and placed in cold water for rapid cooling to terminate the pretreatment reaction. The same processes were used to prepare a control except for adding a pretreatment additive.

Each of the pretreated samples in the reactor was transferred to each of 125 mL Erlenmeyer flask, and 2 mL of citric acid buffer (pH 4.8, 1 M), 1.3 mL of sodium azide (1% aqueous solution), 0.25 mL of Celluclast® 1.5 L (cellulase complex enzyme, Novozymes Korea), 13 μL of Novozyme 188 (β-glucosidase, Novozymes Korea) and distilled water were added thereto. After adjusting the acidity of the mixture to 4.8, a citric acid buffer (50 mM) with a pH value of 4.8 was added to the Erlenmeyer flask to make a total weight of mixture of 40 g. The experiment was repeated 2 times.

The Erlenmeyer flask was placed in a constant temperature shaking apparatus and allowed to react for 72 hours at 50° C. and 200 rpm to hydrolyze carbohydrates (enzymatic saccharification). 1 mL of the reactant was taken, centrifuged, and then the supernatant thus obtained was analyzed by using high-performance liquid chromatography (HPLC) (available from Waters) provided with an Aminex HPX-87H column (Bio-Rad) and a refractive index detector to measure the glucose concentration of the reactant.

An average concentration value was calculated as the amount of glucose obtained based on 100 g of dried sunflower stalk powder, and the results are shown in Table 1 below.

TABLE 1

| Pretreatment additive | Form of additive | Glucose yield (g/100 g sunflower stalk) | % increase as compared to the control |
|---|---|---|---|
| Diatomite | Granule (20~30 mesh) | 28.4 ± 0.3 | 13 |
| Diatomite | Powder (≤250 mesh) | 29.7 ± 0.4 | 18 |
| Fuller's earth | Powder | 28.2 ± 0.6 | 12 |
| Talc | Powder | 27.9 ± 0.1 | 11 |
| Activated carbon | Powder (0.1 g) | 26.9 ± 0.0 | 7 |
| Zeolite | Granule (20~30 mesh) | 26.2 ± 0.4 | 4 |
| None (Control) | — | 25.1 ± 1.0 | — |

As shown in Table 1 above, 25.1 g of glucose based on 100 g of dried sunflower stalk was prepared from the control without the pretreatment additive and showed a yield of 73% based on 34.5 g (100%) of glucose, which is the amount of glucose when all of the celluloses in raw materials have been converted to glucose. On the contrary, the sample pretreated with powdery diatomite during the pretreatment process according to the present invention yielded 29.7 g of glucose at most, which showed an increase of 18% than the control. Further, even the zeolite added sample, which showed the minimal enhancement effects, showed an approximately 4% increase in sugar yield than the no additive sample (control).

Example 2: Pretreatment and Enzymatic Saccharification of Sunflower Stalk in the Presence of Pretreatment Additive (2)

1 g of sunflower stalk powder of known chemical composition was introduced to a small scale reactor having a capacity of 100 mL, and 20 mL of water was added thereto. 1 g of each of the pretreatment additive listed in Table 2 in the form of granules was added to the reactor along with a stir bar then, reactor was sealed, placed in an oil bath, and then heated. When the thermometer placed in the small reactor indicated an initial temperature of 185, the temperature of the reactor was maintained at 185±1° C. for 30 minutes, and then the reactor was removed from the bath and placed in cold water for rapid cooling to terminate the pretreatment reaction. The above procedures were repeated except for not adding silicate mineral to prepare a control.

Each of the pretreated samples in the reactors were transferred to each of 125 mL Erlenmeyer flask, and 2 mL of citric acid buffer (pH 4.8, 1 M), 1.3 mL of sodium azide (1% aqueous solution), 0.5 mL of Celluclast® 1.5 L (cellulase complex enzyme, Novozymes Korea), 25 μL of Novozyme 188 (β-glucosidase, Novozymes Korea) and distilled water were added thereto. After adjusting the acidity of the mixture to 4.8, and a citric acid buffer (50 mM) with a pH value of 4.8 was added to make a total weight of mixture of 40 g. The experiment was repeated 2 times.

The Erlenmeyer flask was placed in a constant temperature shaking apparatus and allowed to react for 72 hours at 50° C. and 200 rpm to hydrolyze carbohydrates. 1 mL of the reactant was taken, centrifuged, and then the supernatant thus obtained was analyzed by using HPLC to measure the glucose concentration of each sample. An average concentration value was calculated as the amount of glucose obtained based on 100 g of dried sunflower stalk powder, and the results are shown in Table 2 below.

TABLE 2

| Pretreatment additive | Form of additive | Glucose yield (g/100 g of sunflower stalk) | % increase as compared to the control |
|---|---|---|---|
| Diatomite | Granule (20~30 mesh) | 30.5 ± 0.6 | 16 |
| Kaolinite | Granule (20~30 mesh) | 28.7 ± 0.3 | 9 |
| Zirconia | Granule (20~30 mesh) | 28.0 ± 0.3 | 6 |
| Glass bead | Granule (diameter: 1 mm) | 27.1 ± 0.3 | 3 |
| Sand | Granule (20~30 mesh) | 27.4 ± 0.0 | 4 |
| Teflon | Granule (diameter: 1 mm) | 27.4 ± 0.0 | 4 |
| None (Control) | — | 26.4 ± 0.0 | — |

As shown in Table 2 above, 26.4 g of glucose based on 100 g of dried sunflower stalk was prepared from the control without a pretreatment additive and showed a yield of 77% based on 34.5 g (100%) of glucose, which is the amount of glucose when all of the celluloses in raw materials have been converted to glucose. On the contrary, the sample pretreated with granulate diatomite according to the present invention yielded 30.5 g of glucose at most, which was increased by 16% than the control. Further, even the glass bead additive, which had the minimal enhancement effects, showed an approximately 3% increase in sugar yield than the no additive sample (control).

Example 3: Pretreatment and Enzymatic Saccharification of Palm Trunk Using Pretreatment Additive The same pretreatment (180° C.) and enzymatic saccharification were performed as in Example 1, except for using a palm trunk purchased from Indonesia instead of a sunflower stalk and the results are shown in Table 3 below.

TABLE 3

| Pretreatment additive | Form of additive | Glucose yield (g/100 g of palm trunk) | % increase as compared to the control |
|---|---|---|---|
| Diatomite | Granule (20~30 mesh) | 45.6 ± 0.8 | 9 |
| Kaolinite | Powder (≤250 mesh) | 43.3 ± 0.1 | 4 |
| Zeolite | Granule (20~30 mesh) | 43.7 ± 0.1 | 5 |
| None (Control) | — | 41.7 ± 0.8 | — |

As shown in Table 3, the glucose yield from the control without a pretreatment additive was 41.7 g at a temperature of 180° C., which is the optimum temperature to release hemicellulose in the palm trunk. However, the glucose yield from the control using the granulate diatomite was 45.6 g, which was increased by 9% from the glucose yield of the control without a pretreatment additive. Further, the sugar yield of the test sample added with the granulate zeolite was increased by 5% than the control. Therefore, it was observed that the treatment method according to the present invention clearly showed enhancement effects in sugar yield.

Example 4: Sugar Yield Enhancement Effects by Pretreatment Additive at Various Temperature Conditions 1 g of sunflower stalk powder was introduced to a small scale reactor having a capacity of 100 mL, and 20 mL of water was added thereto. 1 g of 20~30 meshes of granulate diatomite was added thereto as a pretreatment additive along with a stir bar, then, the reactor was sealed, placed in an oil bath, and then heated. When the thermometer placed in the small scale reactor indicated a desired pretreatment temperature, the temperature of the reactor was maintained at the desired temperature±1° C. for 40 minutes, and then the reactor was removed from the bath and placed in cold water for rapid cooling to terminate the pretreatment reaction. The pretreatment temperatures were set at 170, 180, 190 and 200° C. The same processes were performed to prepare a control, except for adding a granulate diatomite.

Each of the pretreated samples in the reactor above was transferred to each of 125 mL Erlenmeyer flask, and the same method as in Example 1 was used to perform enzymatic saccharification. 1 mL of the reactant was taken, centrifuged, and then the supernatant thus obtained was analyzed by using HPLC to measure the concentration of glucose and the concentration of other sugars including xylose, and an average concentration value was calculated as the amount of glucose obtained based on 100 g of dried sunflower stalk powder. The results are shown in Table 4 below.

at which the glucose yield is maximal. This suggests that all types of sugar including glucose and xylose may be obtained with substantially higher yields by performing only one pretreatment.

Example 5: Acid Pretreatment and Enzymatic Saccharification of Corn Stover or Yellow Poplar Using Pretreatment Additive 1 g of corn stover powder or yellow poplar powder was placed in a small scale reactor having a capacity of 100 mL, and 20 mL of 0.05% sulfuric acid aqueous solution was added thereto. 1 g of 20~30 meshes of granulate diatomite was added thereto as a pretreatment additive along with a stir bar, then, the reactor was sealed, placed in an oil bath, and then heated. When the thermometer placed in the small reactor indicated a desired pretreatment temperature, the temperature of the reactor was maintained at the desired temperature±1° C. for 40 minutes, and then the reactor was removed from the bath and placed in cold water for rapid cooling to terminate the pretreatment reaction. The pretreatment temperatures were set at 170 and 180° C. The same processes were performed to prepare a control except for adding a granulate diatomite.

All of the pretreated samples in the reactor above were transferred to a 125 mL Erlenmeyer flask, calcium carbonate was added thereto to neutralize the sample to pH 4.8, and then enzymatic saccharification was performed by using the method described in Example 1. 1 mL of the reactant was taken, centrifuged, and then the supernatant thus obtained was analyzed by using HPLC to measure the concentration of glucose and the concentration of other sugars including xylose and an average concentration value was calculated as the amount of glucose obtained based on 100 g of corn stover or yellow poplar powders. The results are shown in Table 5 below.

TABLE 5

| Biomass | Pretreatment additive | Pretreatment temperature (° C.) | Glucose yield (g/100 g of biomass) | | % increase as compared to the control |
| --- | --- | --- | --- | --- | --- |
| | | | Pretreated with diatomite | None (Control) | |
| Corn stover | Diatomite | 180 | 31.3 | 28.3 | 11 |
| Yellow poplar | Diatomite | 170 | 38.2 | 34.0 | 12 |

TABLE 4

| Pretreatment additive | Pretreatment temperature (° C.) | Glucose yield (g/100 g of sunflower stalk) | | % increase as compared to the control |
| --- | --- | --- | --- | --- |
| | | Pretreated with diatomite | None (Control) | |
| Diatomite | 170 | 29.7 | 25.4 | 17 |
| | 180 | 32.5 | 27.8 | 17 |
| | 190 | 34.2 | 31.0 | 10 |
| | 200 | 34.9 | 32.1 | 9 |

As shown in Table 4 above, the samples including the granulate diatomite during the pretreatment process in accordance with the present invention showed an increase in sugar yield at all of the pretreatment temperatures than the no additive samples (controls). In particular, it has been observed that the sugar yield was increased by 17% than the control at a temperature of 180° C., which is the temperature As shown in Table 5 above, the samples including the granulate diatomite during the pretreatment process in accordance with the present invention showed an increase in sugar yield at all of the pretreatment temperatures than the no additive samples (controls).

Example 6: Enzymatic Saccharification of Sunflower Stalk Using Saccharification Additive 120 g of sunflower stalk of known chemical composition was introduced to a large scale reactor having a capacity of 2,000 mL (Parr reactor, available from Parr Instrument Co. Ltd., U.S.A.), and 1,380 mL of distilled water was added thereto, and then heated. When a thermometer placed in the reactor indicated an initial temperature of 180° C., the temperature of the reactor was maintained for 40 minutes, followed by rapid cooling to terminate the pretreatment reaction.

The pretreated materials in the reactor were homogenized, and an amount equivalent to 1 g dry weight of the pretreated materials was transferred to a 125 mL Erlenmeyer flask, and 1 g of each of saccharification additives listed in Table 6 (0.1 g for activated carbon) was added to the flask to prepare a mixture. Subsequently, the mixture was agitated for 10 minutes at room temperature, then citric acid buffer was added to the mixture in 50 mM, then sodium azide was added to the mixture and pH of the mixture was adjusted to 5. Thereafter, the flask was placed in a constant temperature shaking apparatus, shaken for 1 hour at a temperature of 50° C., and cooled to room temperature to prepare a cooled product. 0.09 mL of Cellic CTec2 (Novozymes Korea) and 0.01 mL of Cellic HTec2 (Novozymes Korea) were added as hydrolases to the cooled product to perform enzymatic saccharification.

Meanwhile, when 0.2 g of mica was used as a saccharification additive for the homogenized pretreated materials, 0.2 g of the mica was added to the pretreated materials, agitated at a temperature of 90° C. for 10 minutes and sulfuric acid was added thereto to adjust the acidity of the suspension thus obtained to pH 3. The suspension was agitated, cooled down to room temperature, and subjected to enzymatic saccharification by adding a citric acid buffer, sodium azide and an enzyme.

1 mL of the reactant was taken, centrifuged, and then the supernatant thus obtained was analyzed by using HPLC (Waters) provided with an Aminex HPX-87H column (Bio-Rad) and a refractive index detector to measure the glucose concentration of the sample. An average concentration value was calculated as the amount of glucose obtained based on 100 g of dried sunflower stalk powder, and the results are shown in Table 6 below.

TABLE 6

| Saccharification additive | Form of additive | Glucose yield (g/100 g of sunflower stalk) | % increase as compared to the control |
|---|---|---|---|
| Diatomite | Powder (≤250 mesh) | 28.0 ± 0.2 | 18 |
| Fuller's earth | Powder | 29.6 ± 0.3 | 25 |
| Talc | Powder | 26.9 ± 0.1 | 14 |
| Activated carbon | Powder | 26.5 ± 0.4 | 12 |
| Pyrophyllite | Powder | 25.5 ± 0.3 | 8 |
| Zeolite | Powder | 24.2 ± 0.3 | 2 |
| Talc 0.2 g | Powder | 28.0 ± 0.5 | 18 |
| None (Control) | — | 23.7 ± 1.0 | — |

As shown in Table 6 above, only 23.7 g of glucose was obtained from a control sample that has been subjected to enzymatic saccharification without adding a saccharification additive to pretreated materials; however all other samples added with the saccharification additives in the enzymatic saccharification processes of pretreated materials in accordance with the present invention showed higher glucose yields than the no additive sample (control). Particularly, the sample in which Fuller's earth has been added showed increase in sugar yield by 25% than the control, and the sample in which diatomite powder has been added also showed a significant enhancement in the sugar yield. Also, when mica was used as a saccharification additive and agitation temperature and acidity were adjusted, the use of only 0.2 g of the mica increased the sugar yield by 18%, which suggests substantial sugar yield enhancement effects.

What is claimed is:

1. A method of saccharification of biomass before fermenting sugars, the method comprising:

(a) suspending biomass in water or an acidic aqueous solution followed by autohydrolysis or acid pretreatment; and
   (b) subjecting the suspension obtained in step (a) to enzymatic saccharification, before fermentation, by using a cellulase complex enzyme selected from the group consisting of cellulose hydrolase, hemicellulose hydrolase, xylanase, arabinase, β-glucosidase, and mixtures thereof to produce sugars, and
   wherein an additive selected from the group consisting of natural silicate mineral, artificial silicate mineral, zirconia, heat-resistant organic polymer, and a mixture thereof is added in step (b) or both in steps (a) and (b).

2. The method of claim 1, wherein the biomass is used in pulverized or powdered form.

3. The method of claim 2, wherein the pulverized or powdered biomass is derived from the group consisting of: agricultural by-products comprising sunflower stalk, corn stover, bagasse, palm residue, rice straw, barley straw and wheat straw; forest trees and by-products thereof comprising yellow poplar, willow, spruce; and bioenergy crops comprising miscanthus, reed and switchgrass.

4. The method of claim 1, wherein the natural silicate mineral is selected from the group consisting of diatomite, Fuller's earth, mica, kaolinite, talc, pyrophyllite, sand and a mixture hereof.

5. The method of claim 1, wherein the artificial silicate mineral is a powder or granule prepared by mixing one or more of a sintered material prepared by molding the powders followed by sintering at high temperature, a synthetic zeolite or a glass bead, or a mixture of natural silicate minerals with one or more of a sintered material prepared by molding the powders followed by sintering at high temperature, a synthetic zeolite or a glass bead.

6. The method of claim 1, wherein the additive is in the form of a particulate, a powder, or a granulate;
   wherein when the additive is in the powder form, the additive further includes an activated carbon, and
   wherein when the additive is in the granulate form, the additive further includes zeolite.

7. The method of claim 1, wherein the additive is used in an amount ranging from 0.001 to 10 times the weight of dry biomass.

8. The method of claim 1, wherein the additive is added in step (a), and the suspension in step (a) is heated to a temperature ranging from 160 to 230° C., maintained at the temperature for 2 seconds to 24 hours, and then rapidly cooled down to the room temperature.

9. The method of claim 1, wherein the additive is added to the suspension obtained in step (a), and said suspension is stirred in the temperature ranging from room temperature to 100° C. for 2 seconds to 24 hours, adjusted to pH 2 to pH 9 by adding an acid or a base, and then cooled down to 40 to 60° C., followed by adding a hydrolase for saccharification.

10. The method of claim 1, wherein a weight ratio of the biomass to water or an acid aqueous solution in step (a) is about 1:99 to about 20:80.

11. The method of claim 1, wherein the weight ratio of the biomass to water or an acid aqueous solution in step (a) is about 1:99 to about 30:70.

12. The method of claim 1, wherein the additive is the natural silicate mineral.

13. The method of claim 1, wherein the additive is the artificial silicate mineral.

14. The method of claim 1, wherein the additive is the zirconia.

15. The method of claim 1, wherein the additive is the heat-resistant organic polymer.

16. The method of claim 15, wherein the heat-resistant organic polymer is polytetrafluoroethylene.

17. A method of producing a bioalcohol, comprising:
fermenting the sugar produced by the method of claim 1, after step (b), to produce the bioalcohol.

18. The method of claim 17, wherein the bioalcohol is bioethanol.

* * * * *